(12) United States Patent
Gardeski et al.

(10) Patent No.: US 8,142,367 B2
(45) Date of Patent: Mar. 27, 2012

(54) METHOD AND APPARATUS FOR DEFLECTING A SCREW-IN LEAD

(75) Inventors: Kenneth C. Gardeski, Plymouth, MN (US); Corinne A. G. Poor, Roseville, MN (US); William J. Clemens, Fridley, MN (US); Jeremy J. Odegard, River Falls, WI (US)

(73) Assignee: Medtronic, Inc., Minneapolis, MN (US)

( * ) Notice: Subject to any disclaimer, the term of this patent is extended or adjusted under 35 U.S.C. 154(b) by 1012 days.

(21) Appl. No.: 12/037,692

(22) Filed: Feb. 26, 2008

(65) Prior Publication Data
US 2008/0147085 A1   Jun. 19, 2008

Related U.S. Application Data

(60) Continuation of application No. 10/844,746, filed on May 13, 2004, now Pat. No. 7,396,335, which is a division of application No. 09/659,797, filed on Sep. 12, 2000, now Pat. No. 6,805,675.

(51) Int. Cl.
*A61B 5/00* (2006.01)

(52) U.S. Cl. ...................................................... 600/585

(58) Field of Classification Search .................. 600/585, 600/434, 435, 433; 607/116, 119, 122; 604/95.01, 604/95.04
See application file for complete search history.

(56) References Cited

U.S. PATENT DOCUMENTS

| | | | |
|---|---|---|---|
| 3,452,740 A * | 7/1969 | Muller | 600/585 |
| 4,136,703 A | 1/1979 | Wittkampf | |
| 4,215,703 A * | 8/1980 | Willson | 600/585 |
| 4,488,561 A | 12/1984 | Doring | |
| 4,572,605 A | 2/1986 | Hess | |
| 4,676,249 A | 6/1987 | Arenas et al. | |
| 4,815,478 A | 3/1989 | Buchbinder et al. | |
| 4,922,607 A | 5/1990 | Doan et al. | |
| 4,940,062 A | 7/1990 | Hampton et al. | |
| 5,040,543 A | 8/1991 | Badera et al. | |
| 5,170,787 A | 12/1992 | Lindegren | |
| 5,327,906 A | 7/1994 | Fideler | |
| 5,473,812 A | 12/1995 | Morris et al. | |
| 5,662,119 A | 9/1997 | Brennen et al. | |
| 5,728,148 A | 3/1998 | Bostrom et al. | |
| 6,059,739 A | 5/2000 | Baumann | |
| 6,123,699 A | 9/2000 | Webster, Jr. | |
| 6,263,224 B1 | 7/2001 | West | |
| 6,616,628 B2 | 9/2003 | Hayzelden | |

* cited by examiner

*Primary Examiner* — Kevin T Truong
(74) *Attorney, Agent, or Firm* — Carol F. Barry

(57) ABSTRACT

A deflectable stylet system optimized for use in conjunction with a lead of the type having a fixation helix that is screwed into body tissue by rotation of the lead's connector pin is disclosed. The system includes an attachment that is rotatable and longitudinally slidable with respect to the handle of a deflectable stylet. A lead coupled to the attachment may be moved longitudinally with respect to a stylet to account for slight variances in the lead length. In one embodiment, the attachment couples to the lead via a pushbutton mechanism that can be locked to the lead using one hand. The attachment may be rotated to thereby rotate the lead connector. This allows for retraction and extension of a retractable fixation helix, and for further attachment or detachment of a fixation helix to adjacent tissue. In one embodiment, the attachment may be longitudinally rigidly positioned in predetermined locations with respect to the handle. According to another aspect of the system, a deflection device is coupled to the handle to facilitate deflection of the stylet. In one embodiment, this deflection device may be rotatably and/or slidably activated to accomplish the stylet deflection. The system allows a user to adjust lead length with respect to the stylet length, and to further perform stylet deflection and lead rotation all with one hand.

11 Claims, 6 Drawing Sheets

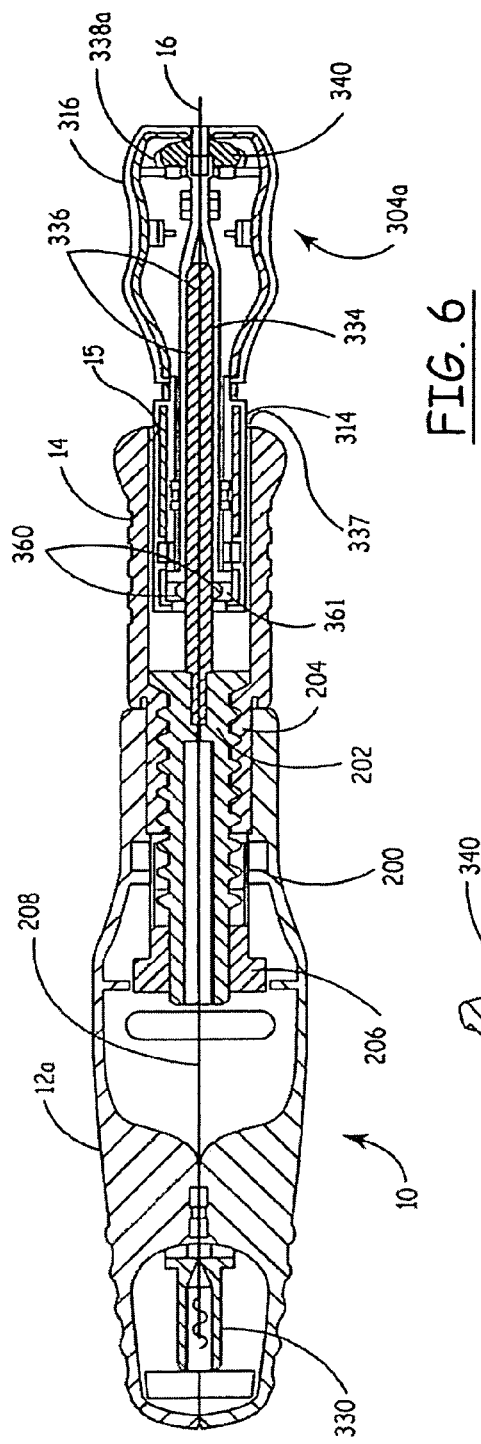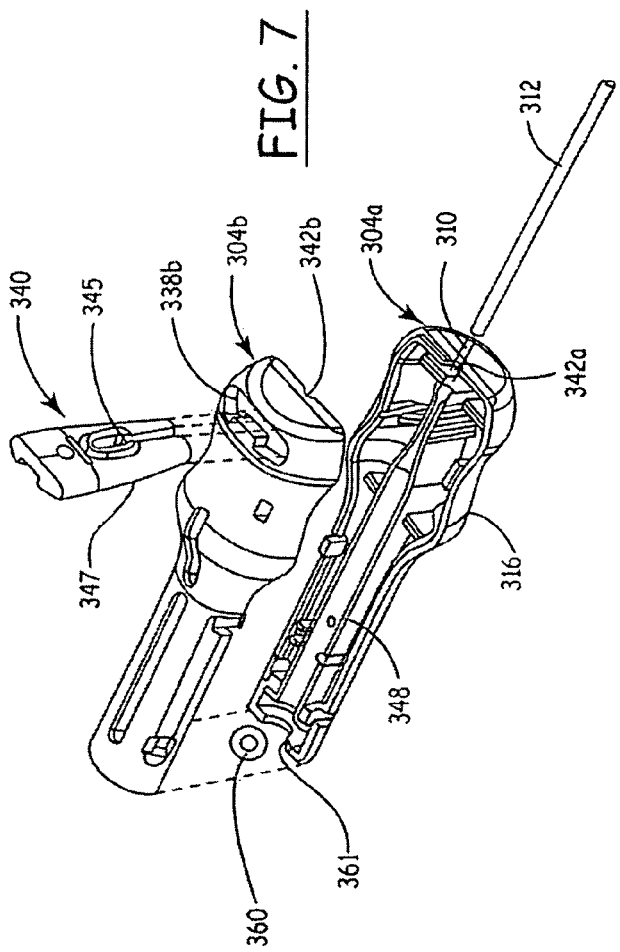
FIG. 6
FIG. 7

METHOD AND APPARATUS FOR DEFLECTING A SCREW-IN LEAD

CROSS REFERENCE TO PRIORITY APPLICATION

This application is a continuation of U.S. patent application Ser. No. 10/844,746, filed May 13, 2004 now U.S. Pat. No. 7,396,335; which is a divisional of U.S. patent application Ser. No. 09/659,797, filed Sep. 12, 2000 now U.S. Pat. No. 6,805,675; both of which are herein incorporated by reference in their entirety.

CROSS REFERENCE TO COMMONLY-ASSIGNED PATENTS

Reference is made to commonly-assigned U.S. Pat. No. 6,059,482, filed May 29, 1998, by Baumann; and to commonly-assigned U.S. Pat. No. 6,027,462 issued to Greene et al, which have related subject matter.

BACKGROUND OF THE INVENTION

The present invention relates generally to implantable leads and catheters and more particularly to mechanisms for deflecting implantable leads and catheters to assist in guiding them through the vascular system.

Over the years, quite a number of mechanisms have been disclosed and employed to deflect catheters and implantable leads. These have taken the form of deflectable guidewires and deflectable stylets, typically operable from the proximal end of the lead or catheter, which controllably impart a curve to the distal portion of the catheter. One group of devices comprise deflectable stylets or guidewires which employ a straight, tubular outer member with a curved inner member, the inner and outer members movable relative to one another. Examples of this type of deflection mechanism are disclosed in U.S. Pat. No. 4,136,703 issued to Wittkampf and U.S. Pat. No. 5,728,148 issued to Bostrom et al. Alternatively, deflection devices employing a curved outer member and a relatively straight inner member are also known to the art, as disclosed in U.S. Pat. No. 4,676,249 issued to Arenas and U.S. Pat. No. 5,040,543 issued to Badera et al. In devices of both types, the relative position of the inner member with respect to the outer member determines the degree to which the curved member (inner or outer) is allowed to display its preset curvature.

A more commonly employed approach to providing controllable deflection employs a generally straight outer member and a tension or push wire located within the outer member that, upon advancement or retraction, causes the outer member to bend. Examples of such deflection mechanisms can be found in U.S. Pat. No. 4,815,478 issued to Buchbinder et al., and U.S. Pat. No. 4,940,062 issued to Hampton et al. Particularly in the context of deflectable stylets intended for use in conjunction with implantable medical leads such as pacing and cardioversion leads, steerable stylets employing this third type of deflection mechanism are disclosed in U.S. Pat. No. 5,662,119 issued to Brennan et al., U.S. Pat. No. 5,170,787 issued to Lindegren, and U.S. Pat. No. 5,327,906 issued to Fideler et al, all of which are incorporated herein by reference in their entireties.

Additional deflectable stylet designs are disclosed in the above-cited Bauman and Greene et al applications. In these designs, the handle for the stylet is provided with a rotatable knob which, like in the above-cited Fideler patent, is employed to curve and straighten the stylet. This knob is provided with a distally facing recess at its distal end. The connector assembly of the lead is located in this distally facing recess.

In conjunction with the use of deflectable stylets to implant leads having screw-in fixation mechanisms which require rotation of the connector pin to screw the fixation mechanism into body tissue, it is also known to employ a spinner ball or clamp to rotate the connector pin, as described in the Pacesetter Locator Steerable Stylet User Manual for the Pacesetter Model 4036 Steerable Stylet. The spinner ball, as described, however, does not allow compensation for variations in lead length or allow for ready adjustment of the position of the stylet within the lead body. For example, the spinner ball mechanism must be disconnected from the handle to allow for retraction of the stylet tip within the lead to reduce the stiffness at the lead tip.

SUMMARY OF THE INVENTION

The present invention is directed toward providing a deflectable stylet system particularly optimized for use in conjunction with a lead of the type having a fixation helix, in which the fixation helix is screwed into body tissue by rotation of the connector pin of the lead. In particular, the invention is intended to provide a deflectable stylet system that allows for differences in length from lead to lead and also provides an easy mechanism for adjusting the position of the stylet within the lead body.

The present invention accomplishes the above results by means of an attachment to the stylet handle which includes an affixation device that may be connected to the connector pin of the lead. In one embodiment, the affixation device may be a threaded device such as a screw. In another embodiment, the affixation device is a pushbutton clevis having an unlocked position for receiving the lead, and a locked position for rigidly coupling the lead to the attachment.

When the attachment is coupled to the lead, the attachment may be rotated to screw the fixation helix into body tissue, configured such that the knob and the lead to which it is attached may readily be moved longitudinally relative to the remainder of the deflectable stylet handle. In a preferred embodiment, the attachment includes a knob with a recess at its distal end for engaging the connector pin of a lead and an elongated tubular extension at its proximal end, slidably inserted into a corresponding distally facing recess in a deflectable stylet handle. In a more preferred embodiment, the distally facing recess in the stylet handle is formed within the spinner or knob of a deflectable stylet handle generally as disclosed in the above cited Greene et al application. The proximally directed extension on the attachment's knob allows for it to be moved longitudinally relative to the stylet handle, in turn allowing for longitudinal movement of the lead relative to the deflectable stylet.

In one preferred embodiment, the deflectable stylet assembly is also provided with a tubular pin, mounted around the proximal portion of the flexible stylet and mounted in fixed longitudinal relationship with the stylet handle. This tubular pin may engage the interior of the proximally directed tubular extension of the attachment, providing for an additional mechanism to allow longitudinal movement of the attachment knob relative to the deflectable stylet handle, while retaining appropriate alignment of the attachment knob and stylet handle to allow for rotation of the attachment knob. In some embodiments, a bushing may be provided within the attachment to facilitate the free rotation of the attachment around the tubular pin. The attachment may be slip-fit to the tubular pin in a manner that provides for controlled longitu-

BRIEF DESCRIPTION OF THE DRAWINGS

FIG. 6 is a cut-away view of another embodiment of the handle assembly and the attachment.

FIG. 7 is a perspective diagram of the embodiment of the attachment illustrated in FIG. 6, and further includes the pushbutton clevis mechanism.

DETAILED DESCRIPTION OF THE PREFERRED EMBODIMENTS

Figure 1:
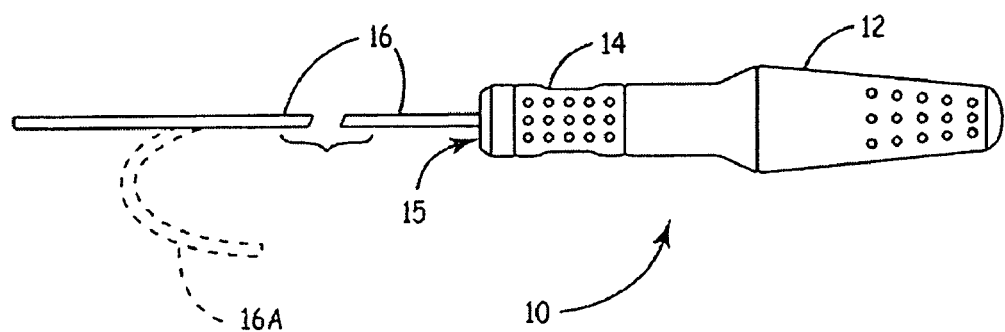
FIG. 1 is a plan view of a prior art deflectable stylet similar to that used in conjunction with the present invention.

FIG. 1 illustrates a plan view of a prior art deflectable stylet, similar to that employed in conjunction with the present invention. The deflectable stylet 16 is provided with a control handle assembly 10 provided with a handle 12 and a deflection control which takes the form of a spinner or knob 14, mounted rotatably and slidably with respect to the handle portion 12. The handle 12 is provided with indentations at its proximal end, as is the spinner or knob 14 to assist the physician in maintaining a grip. Ribbing, knurling or other texturing could of course be substituted. The deflectable stylet 16 exits from a distal recess 15, within spinner or knob 14. The rotation of spinner or knob 14 causes deflection of the distal portion of stylet 16 to a curved configuration as illustrated at 16A.

Deflectable stylet 16 may take the form of any known deflectable stylet employing an outer tubular member and an inner tension wire which, when it applies tension to the distal tip of deflectable stylet 16, causes the tip of the stylet to curve. Appropriate designs for the deflectable stylet 16 include those described in the Brennen et al, Lindegren and Fideler patents and Bauman and Greene et al. applications discussed above. Alternatively, deflectable stylet 16 may be replaced by a deflectable guidewire, for example, as disclosed in the above-cited Buchbinder patent, also incorporated herein by reference in its entirety. In all of these various guidewires and stylets, the basic structure of the deflectable stylet or guidewire consists of a generally straight element, and an internal tension wire coupled to the distal portion of this straight element, and arranged such that upon application of tension to the internal tension wire, the distal portion of the guidewire or stylet exhibits a curved configuration as illustrated in broken outline at 16A.

Figure 2:
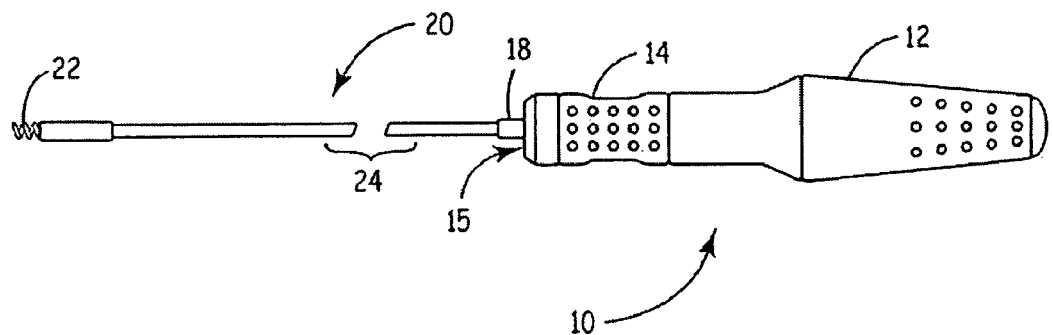
FIG. 2 is a plan view of the deflectable stylet of FIG. 1 shown inserted into an implantable cardiac pacing lead.

FIG. 2 is a plan view of the deflectable stylet of FIG. 1 inserted into a screw-in cardiac pacing lead 20 of a type not requiring rotation of the connector pin relative to the lead body. Cardiac pacing lead 20 comprises an elongated insulated lead body 24 carrying an internal conductor and provided with a connector assembly 18 located at its proximal end, which typically carries a connector pin as is typical of cardiac pacing leads. For example, the distal portion of the connector assembly 18 may correspond to the IS-1 connector standard as disclosed in U.S. Pat. No. 4,922,607 issued to Doan et al., also incorporated herein by reference in its entirety. However, other connector configurations, such as disclosed in U.S. Pat. No. 4,488,561 issued to Doring or U.S. Pat. No. 4,572,605 issued to Hess et al., both also incorporated herein by reference in their entireties, may also be employed. At the distal end of pacing lead 20 is located a fixed helical electrode 22, such as that disclosed in U.S. Pat. No. 5,473,812 issued to Morris et al. and incorporated herein by reference in its entirety, which is screwed into heart tissue in order to stimulate the heart.

As illustrated, the connector assembly 18 of the lead 20 is inserted into the distal facing opening 15 within spinner or knob 14. The spinner or knob 14 is free to rotate with respect to connector assembly 18. Thus, rotation of the spinner knob does not rotate the connector pin of the lead or the lead body itself. However, rotation of the lead body with respect to the deflectable stylet is typically required in order to screw a helical electrode 22 located at the distal end of the lead into heart tissue. Therefore, an alternative mechanism is needed to accomplish the affixation of the helical electrode. This mechanism will be described in detail below.

The above discussion relates to the use of a deflectable stylet in conjunction with an implantable lead. The stylet may further be used with any type of steerable catheter, including an ablation catheter.

Figure 3:
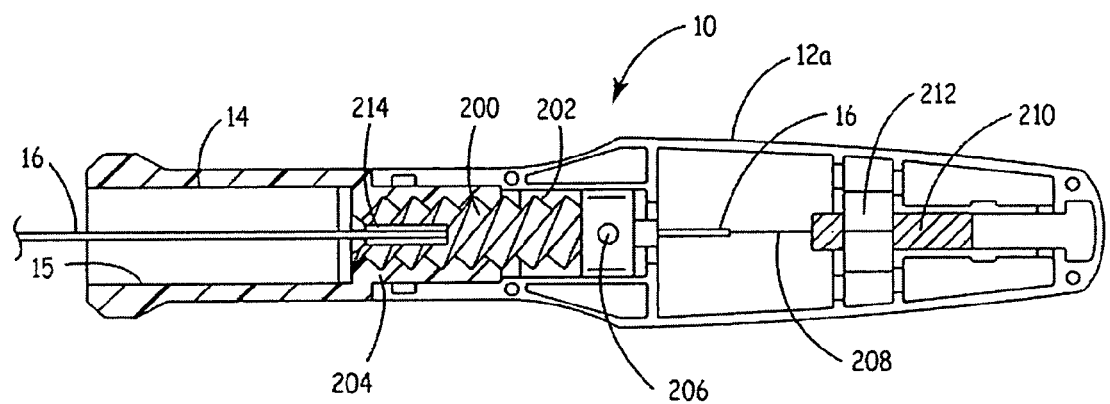
FIG. 3 is a cut-away view through a partially disassembled control handle of one embodiment of the deflectable stylet illustrated in FIG. 1.

FIG. 3 is a cut-away view of a partially disassembled handle assembly 10, as illustrated in the figures discussed above. The handle 12 is fabricated of two molded plastic parts, joined together essentially along a longitudinal line extending the length of the handle. One of the two handle halves 12A is illustrated in conjunction with the knob or spinner 14, showing cross-section and the internal slider 200, not visible in the previous illustrations. The internal, distally facing recess 15 in knob 14 is visible in this view, and is sized to be of sufficient length that it inherently serves as a strain relief to the deflectable stylet 16, preventing kinking or bending of the stylet at the point it exits the slider 200. Recess 15 also assists the physician in repositioning his hand when moving between proximal and distal positions relative to the handle, in that the portion of the connector assembly distal to the connector pin is immediately adjacent the distal end of the knob.

The slider 200 generally takes the form of a rod provided with external threading 202 which engages internal threading 204 within knob 14. At the proximal end of the slider 200 is a collar 206 that engages corresponding grooves in the molded handle halves, not visible in this drawing, to prevent rotation of the slider 200 relative to the handle. Thus, rotation of the knob 14 relative to the handle causes longitudinal movement, but not rotational movement of the slider 200. The outer tube of deflectable stylet 16 is mechanically coupled to the slider 200, while the tension wire 208 within the stylet 16 is anchored to the handle. Thus, on distal movement of the slider 200 relative to the handle 12A, the outer tube of the stylet is moved with respect to the tension wire 208, causing tension wire 208 to apply tension to the tip of the stylet and deflecting it, in the manner described above in the various cited patents pertaining to deflectable stylets. Tension wire 208 is anchored to a threaded rod 210 which is adjusted longitudinally by means of a hex nut 212, which is fixedly mounted in the handle.

As illustrated, the knob 14 and the slider 200 may be longitudinally slid as a unit without rotation in a distal direction with respect to the handle. This provides an alternative mechanism for applying tension to tension wire 208 and deflecting stylet 216. Deflection of the stylet by this mechanism is convenient in the case in which the physician wants to only very briefly and very quickly induce a curve to facilitate entry of the lead into a desired location, for example, into the coronary sinus or for navigating the lead through the vena cava and through the tricuspid valve. Such deflection may be useful for prolapsing the lead in a manner that allows for easy insertion of the lead tip through a valve, for example.

In the embodiment illustrated, the slider is provided with an internal bore 214 which may receive the connector pin of an implantable lead. In this case, the bore 214 should be of larger diameter than the connector pin, so that the lead may be rotated with respect to the stylet 216. Alternatively, the bore 214 may be omitted, with the connector pin simply lying adjacent the distal end of the slider 200.

Figure 4:
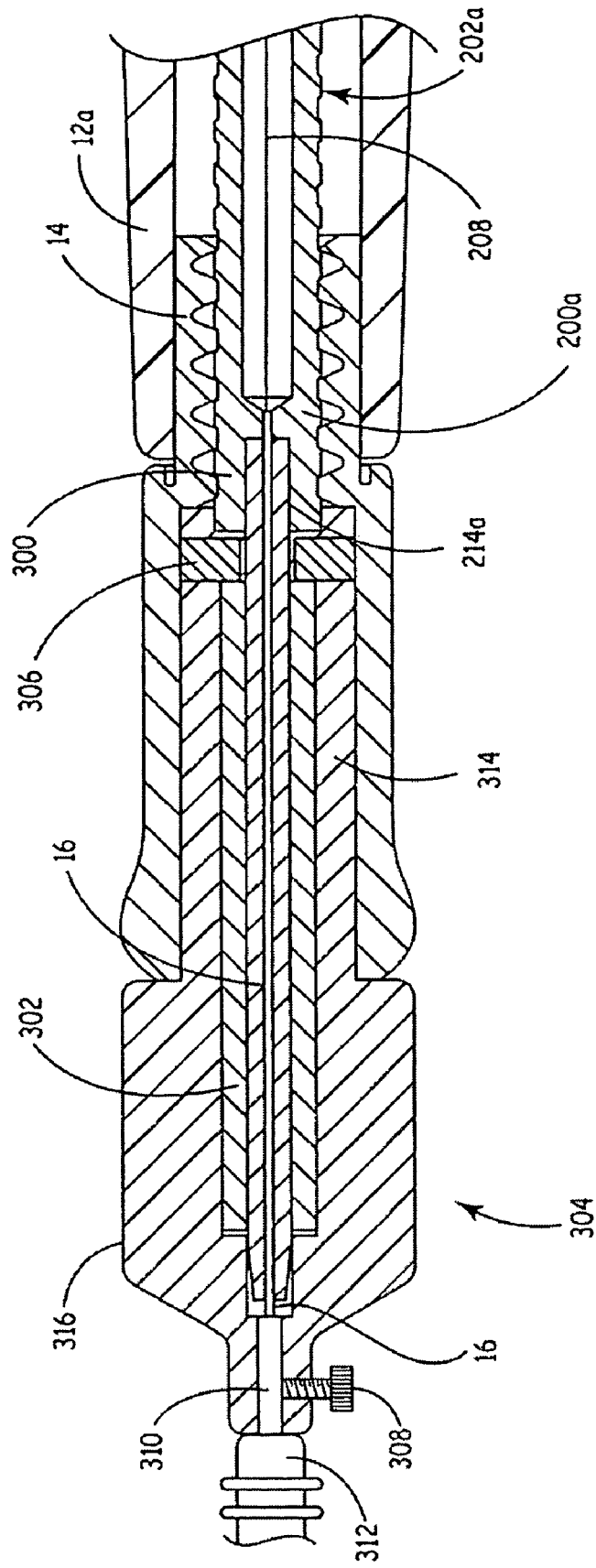
FIGS. 4 and 5 are cut-away views through the distal portion of the handle of a deflectable stylet according to the present invention, with a slip-on attachment according to the present invention and a lead with an advanceable fixation helix in place.

FIG. 4 illustrates a cut-away view through the distal portion of a deflectable stylet handle in conjunction with an attachment according to the invention, to which the connector pin of a lead of the type having a fixation helix is attached. As illustrated, the deflectable stylet control handle corresponds generally to that described in the above cited Greene et al patent and as illustrated in FIGS. 1-3. Handle 12A, knob or spinner 14, deflectable stylet 16 and tension wire 208 correspond to identically numbered components as illustrated in FIGS. 1-3 and discussed above. Slider 200A of this embodiment corresponds generally to slider 200. Operation of the deflectable stylet handle in and of itself is identical to that described above in conjunction with FIGS. 1-3. It may be noted that the embodiment of FIG. 4 shows extending screw threads 202A being cut away in portions. This allows ethylene oxide gas to more easily penetrate the threads during the sterilization process.

Also illustrated is an attachment 304 according to the present invention mounted to the stylet handle. Attachment 304 includes a generally cylindrical knob 316 from which a generally tubular member 314 extends proximally. Tubular member 314 is mounted with a slip-fit to tubular pin 300 within the distal facing recess 15 of knob or spinner 14. The attachment 304 may be slid longitudinally within that recess, and may also be rotated with respect to tubular pin 300.

At the distal end of the attachment 304 is a distally facing bore in which the connector pin 310 of a pacing lead 312 is inserted and is retained by screw 308. Lead 312 may be of the type having a fixation helix, wherein the fixation helix is advanced by rotation of this connector pin 310. Rotation of the fixation helix is discussed further below.

Tubular pin 300 is mounted within recess 214A, in the distal end of slider 200A, and is retained therein frictionally, by adhesive or otherwise. Plug 306 is mounted to the proximal end of the tubular member 314. Located within the proximally extending tubular member 314 of attachment 304 is a bushing 302, which surrounds a tubular pin 300 that is in turn mounted around deflectable stylet 16. Bushing 302 is adhesively or otherwise bonded to the interior of the tubular member 314, and is free to rotate with respect to tubular pin 300. Bushing 302 provides the friction fit between attachment 304 and tubular pin 300 to allow attachment 304 to be slid in a controlled manner along tubular pin 300. Pin 300 thereby allows for an increase in the range of available controlled longitudinal movement of attachment 304 relative to a deflectable stylet handle.

The current invention provides an efficient mechanism for adjusting the position of the stylet 16 within the body of lead in a controlled manner using only a single hand. In contrast, the prior art mechanisms discussed above for adjusting lead position with respect to the stylet require the detachment of the lead from the handle before longitudinal movement of the lead body is possible. In most cases, these prior art mechanisms require two hands to operate, and do not allow for controlled movement of the lead body with respect to the handle.

Figure 5:
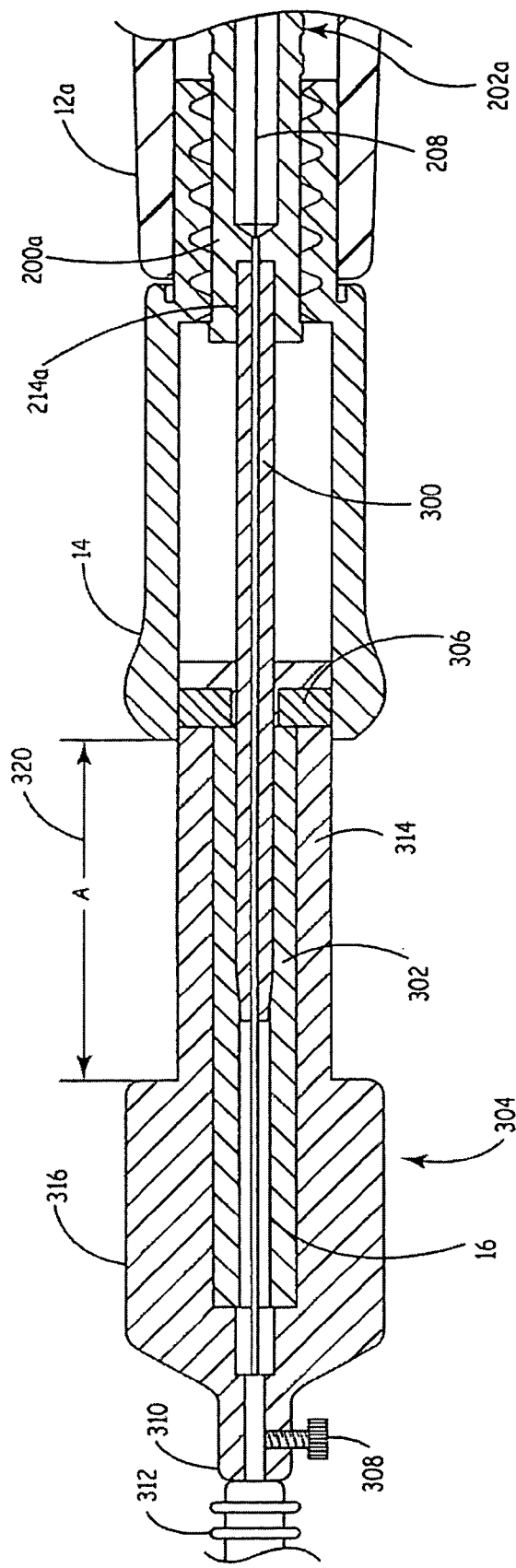

FIG. 5 is a cut-away view of components that are similar to those illustrated in FIG. 4, with all identically numbered components correspond to those in FIG. 4. In this view, attachment 304 is shown advanced distally on tubular pin 300 out of the recess in knob or spinner 14, for a distance "A" which may be, for example, about an inch. Because tubular pin 300 extends distally to the end of knob or spinner 14, it is possible to move the attachment 304 to a point wherein only the proximal most portion of the attachment is located within the recess within spinner or knob 14, while retaining the correct alignment of the attachment with respect to the deflectable guidewire and deflectable guidewire handle.

The current invention may be used to adjust a stylet length to that of a particular lead. The stylet length may be adjusted by a length "A" as shown by extended position 320 of FIG. 5. For example, in some instances, lead lengths may vary by several inches. For leads that are longer, the attachment may be positioned in its most retracted position so that the tip of the stylet is positioned at the end of the lead. For leads that are shorter, the attachment 304 may be positioned at a more extended location within the recess of spinner or knob 14. The attachment therefore allows the flexibility to manufacture longer lead or catheter bodies that may be trimmed and reworked if a defect in the connector is experienced. This reduces overall manufacturing costs, since fewer leads or catheters must be disposed of because of manufacturing defects.

In addition to providing an efficient mechanism for adjusting stylet length, the current invention further provides a mechanism for rotating a helical electrode. As stated previously, the connector pin 310 of a pacing lead 312 is inserted and retained by screw 308 of attachment 304. Therefore, rotation of attachment 304 will result in rotation of the connecting pin and any interconnected helical electrode that is positioned at the distal end of the lead. This allows the helical electrode to be attached to, or detached from, adjacent tissue. It may be noted that the current invention is suitable for use with both retractable and fixed-screw helical electrodes, and is particularly useful when retractable helical electrodes are used.

FIG. 6 is a cut-away view of another embodiment of handle assembly 10 and attachment 304, as illustrated in the figures discussed above. In this Figure, all components corresponding to those in FIGS. 4 and 5 are labeled with the same reference numbers as used in the previous FIGS. 4 and 5 for ease of reference. As in the embodiments discussed above, this embodiment includes a handle fabricated of two molded plastic parts, joined together essentially along a longitudinal line extending the length of the handle. One of the two handle halves shown as 12A is illustrated in conjunction with the knob or spinner 14, shown in cross-section, and the internal slider 200, not visible in the previous illustrations.

The embodiment of the handle shown in FIG. 6 is very similar to that shown in previous FIGS. 4 and 5, with a few exceptions. For example, tension wire 208 is anchored to wire anchor 330, and is not longitudinally adjustable as is the tension wire shown in FIGS. 4 and 5. Instead, tension wire 208 is adhesively bonded or potted into anchor 330 by epoxy for superior tensile strength.

FIG. 6 further illustrates another embodiment of the attachment. As in the embodiments discussed above, the attachment of this embodiment is fabricated of two molded plastic parts, joined together essentially along a longitudinal line extending the length of the handle, with the half of the attachment 304a being shown in FIG. 6. As with the attachment discussed above in reference to FIG. 5, this attachment includes a generally cylindrical knob 316 from which a generally tubular member 314 extends proximally. Tubular member 314 is rotatably mounted to a tubular pin 334 within the distal facing recess 15 of knob or spinner 14 and is also slidable longitudinally within that recess. In this embodiment, tubular member 314 includes a ball-detent coupling mechanism (not shown in FIG. 6) to be described further below. This coupling mechanism is adapted to be rigidly positioned longitudinally with respect to any of the notches 336 included within pin 334. Thus, attachment 304a may be rigidly re-positioned longitudinally at predetermined intervals along at least a predetermined portion of the length of pin 334 while rotating freely in the notches.

This embodiment may further include an elastomeric ring-like structure such as O-ring 360 shown positioned in recess 361. The O-ring allows the attachment to be longitudinally re-positioned at an infinite number of positions using a friction fit with pin 334. O-ring may be used in addition to, or instead of, the ball-detent coupling mechanism discussed below.

Figure 8:
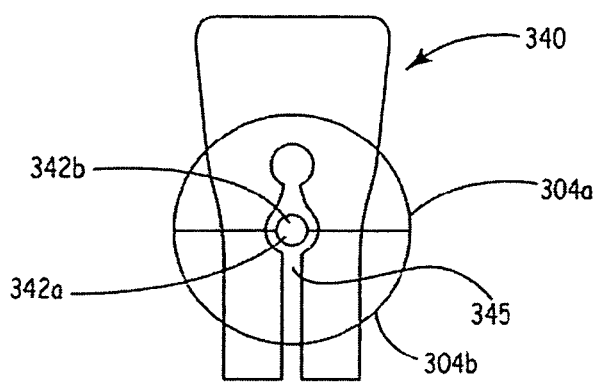
FIG. 8 is a cross-sectional view of the distal end of the attachment illustrating the pushbutton in an unlocked position.
Figure 9:
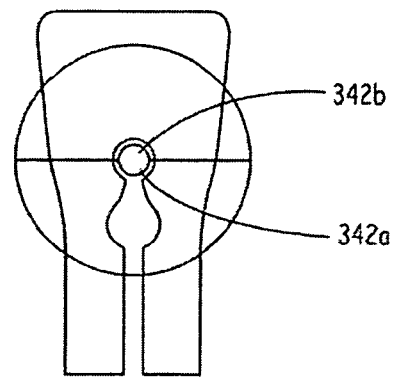
FIG. 9 is a cross-sectional view of the distal end of the attachment illustrating the pushbutton in a locked position.

In the embodiment of FIG. 6, attachment 304a further includes a lead attachment mechanism that uses a pushbutton clevis to fix the lead pin to attachment 304a. FIGS. 8 and 9 each illustrate a cross-section of this pushbutton 340 that resides within a recess 338a and couples the connector pin 310 of a pacing lead 312 to the attachment. The pushbutton clevis is discussed further below. This is an alternative coupling mechanism to screw 308 of FIG. 5. The embodiment of FIGS. 8 and 9 provides the advantage of requiring only a single, one-handed motion to engage and disengage the coupling mechanism as compared to the screw 308 of FIG. 5.

FIG. 7 is a perspective diagram of first and second halves 304a and 304b, respectively, of the attachment of the embodiment of FIG. 6, including pushbutton clevis 340. Pushbutton 340 is adapted to slidably engage within a recess 338b of attachment half 304b, and to further engage in similar recess 338a (shown in FIG. 6) of attachment half 304a when the attachment halves are coupled together as shown by the dashed lines of FIG. 7. The pushbutton is prevented from falling out of recesses 338b by a locking travel limit pin 347 shown protruding perpendicularly from a proximal face of the pushbutton. When inserted within the recess, the pushbutton generally resides in either a first loose position, or a second locked position that will be discussed in more detail below.

Each of the attachment halves further includes a cut-away area 342a and 342b on the distal face of cylindrical knob 316 of attachment halves 304a and 304b, respectively. This cut-away area accommodates the positioning of a lead connector pin 310 of lead 312. When the pushbutton is in the loose position, the connector pin 310 of lead 312 may be easily inserted into this cut-away area. Once the lead connector is so positioned, the pushbutton may be snapped into the locked position such that pushbutton 340 traps connector pin 310 within one end of aperture 345. This fixes the implantable lead 312 in a rigid position with respect to the attachment. Rotation of the cylindrical knob 316 will now rotate the entire lead body, allowing for easy fixation of a helical screw that may be carried at the distal end of the lead body within adjacent tissue. This pushbutton mechanism is further discussed below.

FIG. 7 further shows the coupling mechanism 348 that is provided to couple to notches 336 included within pin 334. In one embodiment, this coupling mechanism is a protrusion 348 that may be included on one or both of the attachment halves 304a and 304b. This protrusion may be, for example, one or more stainless steel balls embedded within a respective wall of one or both of attachment halves 304a and 304b. This protrusion is adapted to fit within any of notches 336 to allow the attachment to be selectably positioned at regular intervals along pin 334. Such a positioning mechanism allows for more controlled positioning of the lead body with respect to the stylet.

In another embodiment, attachment halves 304a and 304b do not include a coupling mechanism such as protrusion 348. Instead, the elastomeric O-ring 360 is positioned in recess 361 between attachment halves 304a and 304b to fit over tubular pin 334 as shown in FIG. 6. The O-ring allows the attachment to be longitudinally re-positioned at an infinite number of positions using a friction fit. Because the O-ring fits loosely within recess 361, the attachment is able to rotate freely about O-ring 360, and therefore also rotate freely around pin 334. In yet another embodiment, both the O-ring 360 and protrusion 348 may be employed in conjunction with tubular pin 334 to provide both longitudinally rigid positioning at discrete intervals, and slipped-fit positioning at locations intermediate the discrete intervals.

FIG. 8 is a cross-sectional view of the distal end of the attachment with halves 304a and 304b coupled together, and further illustrating the pushbutton 340 in a loose position. In this position, a connector pin 310 of lead 312 (not shown in this view) may be easily inserted into the aperture formed by cut-away areas 342a and 342b. A connector pin 310 so inserted is not in intimate contact with aperture 345, and may be easily rotated with respect to the attachment.

FIG. 9 is a cross-sectional view of the distal end of the attachment halves 304a and 304b coupled together, and further illustrating the pushbutton 340 in a locked position. A connector pin 310 of lead 312 (not shown in this view) inserted into the recesses 338a and 338b will be intimate contact with recess 345 so that rotation of the attachment rotates the connector pin 310. When using a lead having a fixed-screw helical electrode, this rotation will rotate the lead body and the helical electrode. When using a lead employing a retractable helical electrode, this rotation will extend or retract the electrode so the helix may be attached to, or detached from, respectively, adjacent tissue.

The attachment of the current invention provides a mechanism for easily manipulating a lead assembly with a single hand. Only a single hand is needed to grasp handle assembly 10, to further rotate or slide knob 14 to deflect a distal tip of a guidewire inserted within a lead, and to rotate attachment 304 to facilitate rotation of the entire lead. Furthermore, using the embodiment of FIG. 7, affixing the lead to attachment 304 may be accomplished with a quick snap of pushbutton 340 that may also be performed with the same hand. This easy, one-handed control system of the current invention thus frees up one hand of the physician for other tasks.

Modifications to the embodiments discussed above are permissible within the scope of the invention, and the possibility of such modification should be understood in conjunction with the claims that follow. For example, in some embodiments, pin 300 might be eliminated, however, in such embodiments, the available range of longitudinal movement of the attachment 304 relative to the deflectable stylet handle would be reduced somewhat. Similarly, in some alternative embodiments, the recess within the knob or spinner 14 might be reduced or eliminated entirely, with the attachment retained in alignment with and mounted to the deflectable stylet handle only by means of tubular pin 300. Similarly, as noted above, other mechanisms for inducing curvature of the deflectable stylet might be substituted for that employed in the handle as illustrated. For example, a knob or handle might be attached directly to the slider 200A, and employed to directly move the slider longitudinally, eliminating the necessity for a rotatable knob. As such, the embodiment illustrated above should be considered as exemplary, rather than limiting, when interpreted in conjunction with the claims which follow.

The invention claimed is:

1. A system for manipulating a lead in conjunction with a deflectable guidewire or stylet, the guidewire or stylet being deflectable by means of a slider attached thereto, the slider being attached to a handle of the system, and the system further comprising:
   an attachment being slidably and rotatably mounted around the deflectable guidewire or stylet, distal to the slider, and comprising means for retaining a proximal end of the lead in which the guidewire or stylet is inserted, such that the attachment and the retained proximal end of the lead can be rotated and slid longitudinally relative to the slider; and
   wherein the handle comprises a distally facing recess, and a portion of the attachment that is mounted around the guidewire or stylet extends within the distally facing recess.

2. The system of claim 1, wherein the handle further comprises a knob coupled to the slider, the knob being rotatable to advance or retract the slider in a longitudinal direction and thereby cause the deflection of the deflectable guidewire or stylet; and the distal facing recess is formed in the knob.

3. The system of claim 1, wherein the means for retaining the proximal end of the lead includes a pushbutton capable of being in a first unlocked position, to receive the proximal end, and in a second locked position, to rigidly couple with the proximal end.

4. The system of claim 1, wherein the means for retaining the proximal end of the lead includes a threaded fastening device.

5. The system of claim 1, further comprising a member adapted to allow the attachment to be rigidly positioned longitudinally at selectable locations relative to the guidewire or stylet and the handle.

6. A system for manipulating a lead in conjunction with a deflectable guidewire or stylet, the guidewire or stylet being deflectable by means of a slider attached thereto, the slider being attached to a handle of the system, and the system further comprising:
   a pin member mounted around the guidewire or stylet distal to the slider; and
   an attachment being slidably and rotatably mounted around the pin member, distal to the slider, and comprising means for retaining a proximal end of the lead in which the guidewire or stylet is inserted, such that the attachment and the retained proximal end of the lead can be rotated and slid longitudinally relative to the slider.

7. The system of claim 6, wherein the handle comprises a distally facing recess in which the pin member and a portion of the attachment that is mounted around the pin member extend.

8. The system of claim 7, wherein the handle further comprises a knob coupled to the slider, the knob being rotatable to advance or retract the slider in a longitudinal direction and thereby cause deflection of the deflectable guidewire or stylet; and the distally facing recess is formed in the knob.

9. The system of claim 6, wherein the means for retaining the proximal end of the lead includes a pushbutton to receive the proximal end, when in an unlocked position, and to rigidly couple with the proximal end, when in a locked position.

10. The system of claim 6, wherein the pin member includes notches interfacing with the attachment thereby allowing the attachment to be rigidly positioned longitudinally at selectable locations along pin member.

11. The system of claim 6, further comprising an O-ring positioned to provide a friction fit between the attachment and the pin.

* * * * *